United States Patent [19]
Mimoun et al.

[11] 4,195,039
[45] Mar. 25, 1980

[54] HETEROGENEOUS PHASE OXIDATION OF OLEFINS TO KETONES

[75] Inventors: Hubert Mimoun, Rueil Malmaison; Robert Charpentier, Villeneuve les Sablons, both of France

[73] Assignee: Institut Francais du Petrole, Rueil-Malmaison, France

[21] Appl. No.: 966,847

[22] Filed: Dec. 5, 1978

Related U.S. Application Data

[62] Division of Ser. No. 838,269, Sep. 30, 1977, Pat. No. 4,155,879.

[30] Foreign Application Priority Data

Sep. 30, 1976 [FR] France ................. 76 29728

[51] Int. Cl.² .................. C07C 27/12; C07C 45/04
[52] U.S. Cl. .................. 260/597 R; 260/586 P; 260/590 R; 260/592; 260/598; 260/599; 260/604 R
[58] Field of Search ......... 260/586 P, 590 R, 592, 260/597 R, 598, 599, 604 R

[56] References Cited

U.S. PATENT DOCUMENTS

| 3,849,480 | 11/1974 | Knowles et al. | 260/586 P |
|---|---|---|---|
| 3,927,111 | 12/1975 | Robinson | 260/604 R |
| 3,946,081 | 3/1976 | Wedemeger et al. | 260/598 |
| 3,965,185 | 6/1976 | Young | 260/590 R |
| 3,998,724 | 12/1976 | Hayes | 252/441 R |
| 4,026,947 | 5/1977 | Costantim et al. | 260/597 R |
| 4,104,310 | 8/1978 | Angstadt | 260/586 P |
| 4,104,312 | 8/1978 | Angstadt et al. | 260/586 P |
| 4,152,354 | 5/1979 | Stapp | 260/597 B |

Primary Examiner—Norman Morgenstern
Attorney, Agent, or Firm—Millen & White

[57] ABSTRACT

Process for manufacturing solid catalysts, useful for oxidizing olefins containing from 2 to 16 carbon atoms per molecule to the corresponding carbonyl derivatives, comprising the step of impregnating a carrier with a substantially non-aqueous solution, containing at least two components [A] and [B] of the general formulas:

$$[A] = M_1 X_n L_m$$

$$[B] = M_2 Z_p L'_q$$

wherein $M_1$ is rhodium or palladium, X and Z are each an anionic group, n and p are integers selected from 1, 2 and 3, m being an integer selected from 1, 2, 3 and 6 or being O, $M_2$ is a metal selected from iron, copper, manganese and cobalt, q is an integer selected from 1 to 6 or is equal to O and L and L' are each a coordinate selected from water or an organic compound, said impregnation being conducted in the presence of at least one halogen, a halohydric acid or an organic or inorganic halide.

8 Claims, No Drawings

HETEROGENEOUS PHASE OXIDATION OF OLEFINS TO KETONES

This is a division of application Ser. No. 838,259 filed Sept. 30, 1977, now U.S. Pat. No. 4,155,879.

This invention relates to an improved process for manufacturing bimetallic catalysts supported on a solid carrier and particularly useful for the conversion of olefins to ketones by means of molecular oxygen.

The process of this invention consists of impregnating a solid carrier with a substantially non-aqueous solution of at least two salts or metal complexes [A] and [B] in the presence of a halohydric acid or an organic or inorganic halide.

The two salts or metal complexes have the following general formula:

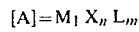

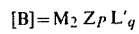

wherein:

$M_1$ is a transition metal selected from rhodium and palladium.

$M_2$ is a transition metal selected from iron, copper, manganese and cobalt.

X and Z are each an anionic group such as a halogen, carboxylate, nitrate, sulfate, perchlorate, thiocyanate or tetrafluoroborate group.

n and p are integers equal to 1, 2 or 3.

m is an integer equal to 1, 2, 3 or 6 or may be equal to 0.

q is an integer selected from 1 to 6 or is equal to 0.

L and L' are each a coordinate selected from water or an organic compound such as dimethylformamide, dimethylsulfoxide, hexamethylphosphorotriamide.

As non-limitative examples of compounds [A] wherein $M_1$ is rhodium, there can be mentioned:

rhodium chloride $RhCl_3, 3H_2O$;
rhodium bromide $RhBr_3, 3H_2O$;
rhodium perchlorate $Rh(ClO_4)_3, 6H_2O$;
$[Rh\ X\ (olefin)_2]_2$
wherein X is chlorine or bromine and the olefin is ethylene, propylene or cycloctene. As example there will be mentioned $[Rh\ Cl\ (C_2H_4)_2]_2$ wherein $C_2H_4$ is ethylene.
$[Rh\ X\ (polyolefin)]_2$
wherein X is chlorine or bromine and the polyolefin is 1,5-cyclooctadiene, 1,5-hexadiene, butadiene or cyclododecatriene. For example there will be mentioned $[Rh\ Cl\ (C_8H_{12})]_2$, wherein $C_8H_{12}$ is 1,5-cyclooctadiene.

In the case where $M_1$ is palladium, the following are non limitative examples of compounds [A]:

Palladium chloride $PdCl_2$
Complex $PdCl_2(C_6H_5CH)_2$
Palladium nitrate $Pd(NO_3)_2$
$PdCl_2$ (diolefin) wherein the diolefin may be, for example, 1,5-cyclooctadiene, 1,5-hexadiene or cyclododecatriene.

As salts or complexes [B] used jointly with compounds of noble metals [A], there can be mentioned as non-limitative examples:

iron, copper, manganese and cobalt perchlorates and nitrates of the general formula $M_2(ClO_4)_2, xH_2O$ with $0 \leq x \leq 6$.

cupric, ferrous or ferric halides of the formula $M_2 Z_p, qH_2O$ with Z=fluorine, chlorine or bromine and $M_2$=iron or copper, p being an integer equal to 2 or 3 and q being either 0 or an integer from 1 to 6.

Complexes such as $M_2Z_p, L'_q$ wherein $M_2$ is iron or copper, Z is a nitrate, perchlorate or halide anion and L' is a coordinate such as dimethyl formamide, hexamethylphosphorotriamide, dimethylsulfoxide.

Examples are as follows:

$CuCl_2 (DMF)_4$;
$CuCl_2 (HMPT)_4$;
$Cu(ClO_4)_2 (HMPT)_4$;
$Cu(NO_3)_2 (HMPT)_4$;

The impregnation of the solid carrier is performed with a substantially non-aqueous solution of the two metal components [A] and [B] of the catalyst.

As a matter of fact, it has been observed that the use of an organic solvent as impregnation medium of the carrier results in catalysts at the surface of which both metals $M_1$ and $M_2$ are associated by couples, this association resulting in a particularly high activity and stability of the catalysts.

As solvents used for impregnating the two components [A] and [B] on the solid carrier, there can be mentioned:

Linear or branched alcohols or polyols containing from 1 to 20 carbon atoms per molecule. The alcohol may be a primary, secondary or tertiary monoalcohol.

The polyol contains at least two alcohol groups.

Examples of impregnation solvents are as follows: methanol, ethanol, n-propanol, isopropanol, 2-butanol, 3—3 dimethyl 2-butanol, 1,2 or 3-pentanols.

There can also be used such polyols as ethylene glycol, propylene glycol as well as glycols mono-or polyethers of the formula $R-O-CH_2-CH_2OH$ wherein R is a hydrocarbon radical and particularly a compound of the formula $CH_3O-CH_2-CH_2OH$.

Particularly convenient impregnation solvents are ketones such as, for example, acetone or methylethylketone and such esters as ethyl and methyl acetates.

It is strictly necessary that the impregnation be performed in the absence of water or at least that the impregnation solvent contain no more than 1% of water by weight. The presence of water in an amount higher than 1% in the impregnation solvent results in the production of catalysts having a substantially lower activity. Ideal conditions would be to proceed in the presence of a perfectly anhydrous solvent.

For this purpose, it may be convenient to add to the medium a dehydrating agent such as a ketal or an acetal. Thus, there can be used 2,2'-dimethoxy propane or 2,2'-diethoxy propane, which products immediately react with any water traces of the medium, if any; it results in that no water traces can be observed by gaseous chromatographic analysis.

In addition to the two metal components [A] and [B], it is necessary to introduce in the impregnating non-aqueous solvent at least one halogen, halohydric acid or organic or inorganic halide.

The presence of the latter results, as a matter of fact, in a very large dispersion of the two metals $M_1$ and $M_2$ over the catalyst, said metals being further associated to the carrier. There is preferably used 1 to 40 moles and, more preferably, 5 to 15 moles of halohydric acid or halogen or halide per rhodium or palladium atom.

Among the halogen compounds, there can be mentioned: hydrochloric acid in anhydrous form, hydrobromic acid, gaseous chlorine, lithium, sodium, or ammonium chlorides as well as hydrocarbon halides such as $CCl_4$, $CHCl_3$ or $CH_2Cl_2$. There will be preferably used anhydrous hydrochloric acid.

The catalyst carrier of the invention contains for example at least one oxide of an element from groups II, III and IV of the periodic classification of elements. Examples are alumina, silica, silica-alumina, magnesia, silica-magnesia, alumina-magnesia; active carbon may also be used, etc. . .

A particularly suitable carrier is alumina.

The specific surface of the carrier may be advantageously from 50 to 600 $m^2/g$ and preferably from 100 to 400 $m^2/g$.

It is particularly convenient to dry the carrier before impregnation; this can be performed by heating the carrier at a temperature from 200° to 500° C., preferably under air scavenging.

The so-dried carrier may be impregnated, for example, with an alcoholic solution of the two components [A] and [B] with the addition thereto of an alcoholic solution of hydrochloric acid. It is also possible to pre-impregnate the carrier with an alcoholic solution of the component [B], for example for 24 hours, to dry the resulting catalyst under vacuum and to impregnate it with a hydrochloric solution of the component [A] in alcoholic medium.

The resulting catalysts are separated from the impregnation solution, washed, for example, with alcohol and dried preferably under vacuum. It is generally not convenient to dry the obtained catalysts at a temperature higher than 150° C. The drying step will, accordingly, be preferably conducted in the range of 0°–150° C.

The molar ratio B/A during the impregnation is generally from 1 to 20 and preferably from 5 to 10.

The molar ratio haloben /[A] during impregnation is generally from 1 to 40 and more preferably from 5 to 15, as above mentioned.

The catalyst of the invention preferably contains, by weight, in proportion to the catalyst carrier, from 0.005 to 1%, and particularly from 0.1 to 0.9% of rhodium or palladium, from 0.1 to 3% and particularly from 0.2 to 1% of one of the metals $M_2$ as above mentioned, i.e. copper, iron, cobalt or manganese.

The catalyst further comprises from 0.1 to 10% and preferably, from 0.2 to 5%, by weight with respect to the catalyst carrier, of halogen, for example chlorine.

The catalyst of the invention may be used for oxidizing in heterogeneous phase (liquid-solid or gaseous-solid) olefins to carbonyl derivatives by means of a gas containing molecular oxygen.

The present invention is applicable to olefinic compounds, branched or unbranched, containing from 2 to 16 carbon atoms per molecule, having the general formula $R_1-CH=CH-R_2$ wherein $R_1$ and $R_2$, similar or different, are either hydrogen atoms or alkyl, aryl, alkylaryl or aralkyl monovalent radicals, each comprising from 1 to 14 carbon atoms, or form together a single bivalent radical.

The terminal primary olefins used preferably according to the invention, i.e. these of the above-mentioned general formula, wherein $R_1=H$ and $R_2$=alkyl, aryl, alkylaryl or aralkyl, contain from 3 to 16 carbon atoms per molecule and produce methylketones selectively. They are olefins of the formula $R_2-CH=CH_2$.

Ethylene gives ethanol.

As non-limitative examples or olefins which can be oxidized to carbonyl derivates according to the process, there can be mentioned: ethylene, propylene, butene, pentenes, hexenes, heptenes, octenes, nonenes, decenes, dodecenes as well as cyclopentane, cyclohexene, cyclooctene and styrene.

The olefins may be used either pure or diluted with other inert or olefinic hydrocarbons. Thus the oxidation of partially hydrogenated steam-cracking $C_4$ cuts, containing a mixture of olefins such as 1-butene and cis and trans 2-butenes as well as butane, results in the selective formation of methylethylketone, butyraldehyde being only obtained as traces.

This high selectivity of the above-described catalysts for the conversion of olefins to ketones, is also to be found in the case of heavy olefins. Thus the oxidation of 1-octene with molecular oxygen in liquid phase and in the presence of rhodium-copper catalysts supported on alumina, results in the exclusive formation of 2-octanone.

The oxidation reaction is conducted in heterogeneous phase, either in liquid phase or in gaseous phase.

In the case where the operation is conducted in liquid phase, the supported catalyst may be suspended in the olefin and oxygen is then introduced. Oxygen absorption and the formation of the corresponding ketone are observed. The operation may also be conducted in fixed bed with the liquid olefin passing over the catalyst; the formation of ketone in the liquid effluent at the outlet from the reactor is then observed.

In the case where the operation is conducted in the gaseous phase, a gaseous mixture of olefin (ethylene, propylene or butene for example) with oxygen or air is passed over the catalyst and the product recovered in the outflow consists of the unreacted olefin and oxygen and of the formed carbonyl compound.

The reaction temperature is generally from about 0° C. to about 150° C., preferably from 30° C. to 130° C.

The oxidizing gas consists of air or pure oxygen or oxygen diluted with nitrogen or with another inert gas. The partial oxygen pressure will preferably be from 0.1 to 25 bars.

Although it is necessary to prepare the catalyst in a substantially anhydrous solvent, the oxidation reaction may be performed in the presence of water. The water content of the medium may be from 0.01% to 50% by weight of the charge. In the case where the operation is conducted in the presence of water, it is advantageous that the latter be in the gaseous form when contacting the catalyst. As a matter of fact, the presence of liquid water on the catalyst tends to occlude its pores and reduce accordingly its activity.

The present invention will be illustrated by the following examples:

EXAMPLE 1

The catalyst is prepared by impregnating 100 g of dry alumina having a specific surface of 227 $m^2/g$ and a pore volume of 62 cc/g, with 500 cc of a solution of:
10 millimoles of rhodium chloride $RhCl_3, 3H_2O$;
20 millimoles of cupric chloride, and;
100 millimoles of gaseous anhydrous hydrochloric acid in anhydrous methanol.

Contact is maintained for 24 hours and then the resulting catalyst is filtered, washed with absolute ethanol and dried under high vacuum at 60° C.

The so-obtained catalyst contains 0.7% of rhodium, 0.3% of copper and 3.5% of chlorine.

In a heat-insulated glass reactor, there is introduced 10 g of crushed catalyst and 50 cc of 1-octene. The reactor temperature is brought to 75° C. Pure oxygen is then introduced in the free portion of the reactor so that the total pressure be 1.2 bars. The contents of the reactor are stirred with a magnetic stirrer and it is observed that the oxygen pressure decreases in the reactor, this pressure decrease being compensated by a permanent addition of fresh pure oxygen.

After 4 hours of reaction, and with an amount of absorbed oxygen of 0.6 mole/liter, there is formed 0.68 mole/liter of 2-octanone corresponding to a molar selectivity of 98%.

EXAMPLE 2 (comparative)

The catalyst is prepared under the same conditions as in example 1 except that the impregnation is conducted in aqueous phase instead of proceeding in anhydrous ethanol. 1-octene is oxidized under the same conditions as in example 1.

After 4 hours of reaction, 0.4 mole/liter of 2-octanone is formed; the molar selectivity is 90%.

This example shows that catalysts impregnated in aqueous phase perform clearly less satisfactorily than the catalysts impregnated in alcoholic phase.

EXAMPLE 3 (comparative)

The catalyst is prepared under the same conditions as in example 1 except that the impregnation is conducted in anhydrous ethanol in the absence of hydrochloric acid.

1-octene is oxidized under the same conditions as in example 1.

After 4 hours of reaction, 0.3 mole/liter of 2-octanone is formed; the molar selectivity is 90%.

This example thus shows that the presence of an acid halogen compound in the impregnation step is necessary to obtain highly selective catalysts.

EXAMPLES 4 to 7

These examples are concerned with the effect of the nature of the carrier in the manufacture of catalysts for oxidizing 1-octene.

| EXAM-PLE | CARRIER | $RhCl_3$ mmole/g carrier | $CuCl_2$ mmole/g carrier | Anhydrous HCl mmole/g carrier | Absorbed $O_2$ in 4 hours mole. $l^{-1}$ | Formed 2-octanene mole. $l^{-1}$ | Molar selectivity |
|---|---|---|---|---|---|---|---|
| 4 | $\gamma$ alumina $S = 194 m^2/g$ | 0.1 | 0.2 | 1 | 0.6 | 1.26 | 98 |
| 5 | Alumina $S = 67 m^2/g$ | 0.1 | 0.2 | 1 | 0.34 | 0.62 | 97 |
| 6 | Active carbon | 0.1 | 0.2 | 1 | 0.06 | 0.12 | 95 |
| 7 | Silica | 0.1 | 0.2 | 1 | 0.02 | 0.04 | 90 |

S = specific surface
mole. $l^{-1}$ = mole/liter.

The catalysts used in experiments 4 to 7 are obtained by impregnation according to the method described in example 1.

The amounts of Rh $Cl_3$, Cu $Cl_2$ and H Cl per gram of carrier are the same. The impregnating solvent is anhydrous ethanol.

Oxidation of 1-octene is conducted as in example 1.

It is observed that alumina is the best carrier for the manufacture of a catalyst for oxidizing olefins to ketones.

EXAMPLES 8 TO 11

$\gamma$-alumina having a 200 m$^2$/g specific surface is impregnated with an anhydrous ethanolic solution of the two components [A] and [B] reported in the following table, also containing anhydrous gaseous hydrochloric acid. The oxidation of 1-octene is conducted as in example 1.

| EXAM-PLE | CARRIER | [A] 0.1m M/g (mM: millimole | [B] 0.2 m M/g | H Cl m M/g | Absorbed $O_2$ mole. $l^{-1}$ | z-Octanone Formed in 4 hours mole. $l^{-1}$ | Molar Selectivity % |
|---|---|---|---|---|---|---|---|
| 8 | $Al_2O_3$ | Rh $Cl_3$ | Fe $Cl_3$ | 1 | 0.4 | 0.76 | 97 |
| 9 | $Al_2O_3$ | Rh Cl (COD)$_2$ | Cu $Cl_2$ | 1 | 0.5 | 1 | 98 |
| 10 | $Al_2O_3$ | Rh $(NO_3)_2$ | Cu $Cl_2$ | 1 | 0.45 | 0.8 | 98 |
| 11 | $Al_2O_3$ | $\left[\begin{array}{c} Rh\ Cl \\ (C_2H_4)_2 \end{array}\right]_2$ | Cu $Cl_2$ | 1 | 0.35 | 0.7 | 98 |

*COD = cyclooctadiene

It is observed that several couples of active supported catalytic systems may be used in the oxidation of olefins to ketones.

EXAMPLE 12

In a tubular reactor, there is introduced 5 g of rhodium-copper catalyst whose preparation has been described in example 1. The reactor temperature is brought to 105° C. On this catalyst, there is passed a mixture of propylene (flow rate=1.5 l/h) and of oxygen (flow rate=0.75 l/h).

The reactor outlet is connected to a gaseous phase chromatograph used for analyzing continuously the effluent. It is observed that 20% of the propylene has been converted with a molar selectivity of 99.4% to acetone and 0.6% to propionaldehyde.

EXAMPLE 13

The oxidation catalyst is prepared by impregnating 100 g of dry alumina having a specific surface of 277 m$^2$/g and a pore volume of 62 cc/g with 500 cc of an anhydrous ethanolic solution containing:

10 millimoles of palladium chloride Pd Cl$_2$;
80 millimoles of cupric chloride;

The carrier is γ alumina having a specific surface of 227 m$^2$/g.

| Ex. | A 0.1 mM/g | B 0.5 mM/g | HCl mM/g | Anhydrous solvent | Converted propylene % | Acetone production g/geata/h | Selectivity to acetone (molar) |
|---|---|---|---|---|---|---|---|
| 18 | Pd Cl$_2$ | Cu(NO$_3$)$_2$ | 1 | Ethanol | 20 | 0.14 | 98.5 |
| 19 | Pd Cl$_2$ (C$_6$H$_5$CN)$_2$ | Cu(ClO$_4$)$_2$ | 1 | Ethanol | 18 | 0.13 | 98.4 |
| 20 | Pd(NO$_3$)$_2$ | Cu Cl$_2$ | 1 | Ethanol | 24 | 0.18 | 98.6 |
| 21 | Pd(NO$_3$)$_2$ | Fe Cl$_3$ | 1 | Ethanol | 21 | 0.15 | 98.3 |

100 millimoles of anhydrous gaseous hydrochloric acid.

The contact is maintained for 24 hours and then the obtained solid catalyst is filtered, washed with absolute ethanol and dried under high vacuum at 60° C.

5 g of the so-obtained catalyst is introduced into a heat-insulated tubular reactor brought to 105° C., at the inlet of which is performed a preheating of the input products by means of carborundum balls.

The reactor is then fed with 1.5 l/h of propylene, 0.75 l/h of oxygen and 1 cc/h of distilled water introduced by means of a micrometric syringe pump.

The contact time is 4 seconds. At the reactor outlet, it is observed that 35% of the propylene has been converted with a molar selectivity of 99.3% to acetone and 0.7% to propionaldehyde.

The production of acetone per gram of catalyst and per hour is 0.25 g.

The activity of the catalyst remains substantially constant over a period of 40 h.

EXAMPLES 14 TO 18

The procedure is conducted as in example 13 with different catalysts whose preparation is reported in the following table. These examples illustrate the effect of the impregnating solvent on the activity and the selectivity of the so-obtained supported catalyst in propylene oxidation.

The carrier is γ alumina having a specific surface of 227 m$^2$/g.

| EXAMPLE | Pd Cl$_2$ mM/g | Cu Cl$_2$ mM/g | Anhydrous HCl mM/g | Impregnating solvent | Converted propylene % | Acetone production g/geata/h | Selectivity to acetone (molar) |
|---|---|---|---|---|---|---|---|
| 14 | 0.1 | 0.2 | 1 | Ethanol* | 23 | 0.17 | 98.7 |
| 15 | 0.1 | 0.2 | 1 | Methanol* | 15 | 0.10 | 98.9 |
| 16 | 0.1 | 0.2 | 1 | Isopropanol* | 14 | 0.10 | 98.6 |
| 17 | 0.1 | 0.2 | 1 | H$_2$O | 1.9 | 0.05 | 98.3 |

*anhydrous.

The oxidation is conducted at 105° C. with 5 g of catalyst, the feeding rates of the reactor in propylene, oxygen and water are respectively 1.5 l/h, 0.75 l/h and 1 cc/h.

These examples show that the impregnation in anhydrous alcoholic phase results in catalysts which are much more active than the catalyst impregnated in aqueous phase.

EXAMPLES 18 to 21

The procedure is the same as in example 13 but with the use of different catalytic systems deposited on alumina and impregnated in anhydrous ethanolic phase in the presence of anhydrous gaseous H Cl.

The oxidation of propylene is conducted as in example 13 at 105° C. with respective flow rates of 1.5 l/h of propylene, 0.75 l/h of oxygen and 1 cc/h of water. These examples show that active oxidation catalyst may be formed by co-impregnation of different metal couples.

EXAMPLE 22

1-butene is oxidized in the presence of the catalyst described in example 13 and under the same conditions: temperature: 105° C.; catalyst: 5 g, 1-butene: 1.5 l/h; oxygen 0.75 l/h; H$_2$O: 1 cc/h.

It is observed at the outlet that 15% of the 1-butene is converted to 2-butanone with a molar selectivity of 98%. There is also formed 1.5% of butyraldehyde. The production of Z-butanone is about 0.12 g per gram of catalyst and per hour.

EXAMPLE 23

Example 13 is repeated except that propylene is replaced by a steam-cracking C$_4$ cut containing by weight 23% of butane, 53% of 1-butene, 14.1% of trans 2-butene and 9.6% of cis 2-butene.

At the reactor outlet it is observed that 30% of the initial 1-butene has been converted to methylethylketone with a molar selectivity of 98%. Cis and trans 2-butenes are oxidized to a very small extent under the reaction conditions.

What we claim is:

1. A process for oxidizing olefins to carbonyl derivatives in heterogeneous phase, by means of a gas containing molecular oxygen, said olefins containing from 2 to 16 carbon atoms per molecule and having the general formula R$_1$—CH=CH—R$_2$ wherein R$_1$ and R$_2$ are independently selected from the group consisting of hydrogen, alkyl, aryl, alkylaryl and aralkyl, or form together a bivalent radical, said process being conducted in the presence of a catalyst prepared according to a process consisting essentially of the steps of impregnating a carrier with a substantially non-aqueous solution having not more than 1% by weight of water, consisting essentially of an organic impregnating solvent having dissolved therein at least two components [A] and [B] of the general formula:

$$[A] = M_1X_nL_m$$

$$[B] = M_2Z_pL'_q$$

the molar ratio of [B]:[A] being 1:1 to 20:1, wherein $M_1$ is rhodium or palladium; X and Z are each an anionic group selected from a carboxylate, a nitrate, a sulfate, a perchlorate, a thiocyanate and a tetrafluoborate; n and p are integers selected from 1, 2 and 3, m being an integer selected from 1, 2, 3 and 6 or being O; $M_2$ is a metal selected from iron, copper, manganese and cobalt; q is an integer selected from 1 to 6 or is equal to O; L is a coordinate selected from water, an olefin, a polyolefin and benzonitrile and L' is a coordinate selected from water, dimethylformamide, hexamethylphosphorotriamide and dimethylsulfoxide and 1 to 40 moles of at least one halogen containing compound per rhodium or palladium atom, said halogen-containing compound being halogen, a halohydric acid, a lithium, sodium or ammonium chloride, carbon tetrachloride, chloroform or methylene chloride; and drying the resultant catalyst at a temperature not higher than 150° C.

2. A process for oxidizing olefins according to claim 1 wherein $M_2$ represents only one metal.

3. A process for oxidizing olefins according to claim 2 wherein $M_2$ represents copper.

4. A process for oxidizing olefins according to claim 2, said catalyst consisting essentially of, by weight, in proportion to the catalyst carrier, 0.1 to 0.9% rhodium or platinum, 0.2 to 1% of $M_2$, and 0.2 to 5% of chlorine.

5. A process for oxidizing olefins according to claim 4, wherein $M_2$ is copper.

6. A process for oxidizing olefins according to claim 1, wherein the organic impregnating solvent is an alcohol, a glycol, or a ketone, said solvent containing from 1 to 20 carbon atoms per molecule and having no trace of water as observed by gaseous chromatographic analysis.

7. A process for oxidizing olefins according to claim 6, wherein the halogen-containing compound is hydrochloric acid.

8. A process for oxidizing olefins according to claim 1, wherein the catalyst carrier is alumina and there is employed 1 to 40 moles of anhydrous hydrochloric acid, as the halogen-containing compound, per atom of rhodium or palladium.

* * * * *